(12) United States Patent
Charlebois et al.

(10) Patent No.: US 10,058,437 B2
(45) Date of Patent: Aug. 28, 2018

(54) SURFACE STRUCTURE OF A COMPONENT OF A MEDICAL DEVICE AND A METHOD OF FORMING THE SURFACE STRUCTURE

(71) Applicant: Cook Medical Technologies LLC, Bloomington, IN (US)

(72) Inventors: Steven J. Charlebois, West Lafayette, IN (US); W. Kurt Dierking, Louisville, KY (US); David E. Orr, Piedmont, SC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 21 days.

(21) Appl. No.: 14/869,085

(22) Filed: Sep. 29, 2015

(65) Prior Publication Data
US 2016/0015535 A1    Jan. 21, 2016

Related U.S. Application Data

(62) Division of application No. 12/936,490, filed as application No. PCT/US2009/039595 on Apr. 6, 2009, now Pat. No. 9,173,983.
(Continued)

(51) Int. Cl.
*A61L 31/02* (2006.01)
*A61L 31/08* (2006.01)
(Continued)

(52) U.S. Cl.
CPC .............. *A61F 2/82* (2013.01); *A61L 31/022* (2013.01); *A61L 31/082* (2013.01);
(Continued)

(58) Field of Classification Search
CPC ...... A61F 2/06; A61F 2/07; A61F 2/24; A61F 2/82; A61F 2/915; A61F 2002/075;
(Continued)

(56) References Cited

U.S. PATENT DOCUMENTS 5,130,192 A * 7/1992 Takabayashi ...... C08G 73/1007
427/209
5,690,670 A    11/1997 Davidson
(Continued)

FOREIGN PATENT DOCUMENTS

EP    1035230 A1    9/2000

OTHER PUBLICATIONS

Pelton, A.R.; Duerig, A.R. (eds). "Fatigue Testing of Diamond-Shaped Specimens," *SMST-2003 Proceedings of the International Conference on Shape Memory and Superelastic Technologies*, SMST Society, Inc. 2004, Menlo Park, CA, 1-8.
(Continued)

*Primary Examiner* — Seema Mathew
(74) *Attorney, Agent, or Firm* — Brinks Gilson & Lione

(57) ABSTRACT

A method of forming a surface structure of a component of a medical devices includes forming a fatigue-resistant portion, which entails forming a first layer comprising a transition metal selected from the group consisting of Ta, Nb, Mo, V, Mn, Fe, Cr, Co, Ni, Cu, and Si on at least a portion of a surface of the component, where the surface comprises a nickel-titanium alloy, and alloying the transition metal of the first layer with the nickel-titanium alloy of the surface. The method further includes forming a rough outer surface of the fatigue-resistant portion, where the rough outer surface is adapted for adhesion of a material thereto.

7 Claims, 4 Drawing Sheets

Related U.S. Application Data

(60) Provisional application No. 61/043,279, filed on Apr. 8, 2008.

(51) Int. Cl.

| | | |
|---|---|---|
| *A61L 31/14* | (2006.01) | |
| *A61F 2/82* | (2013.01) | |
| *C22F 1/00* | (2006.01) | |
| *C22F 1/10* | (2006.01) | |
| *C23C 16/56* | (2006.01) | |

(52) U.S. Cl.
CPC .............. *A61L 31/088* (2013.01); *A61L 31/14* (2013.01); *C22F 1/006* (2013.01); *C22F 1/10* (2013.01); *C23C 16/56* (2013.01); *A61F 2210/00* (2013.01); *A61F 2210/0076* (2013.01); *A61F 2240/00* (2013.01); *A61L 2400/18* (2013.01); *A61L 2420/02* (2013.01); *A61L 2420/08* (2013.01)

(58) Field of Classification Search
CPC .. A61F 2002/30677; A61F 2002/30922; A61F 2002/3631; A61F 2002/368; A61F 2250/0042; A61F 2/848; A61F 2/86; A61F 2/90; A61F 2/958; A61F 2310/00892; A61F 2310/00898; A61F 2/2403; A61F 2/2406; A61F 2/2421; A61F 2/244; A61F 2/2442; A61F 2/2448; A61F 2/30767; A61F 2/367; A61F 2/3859; A61F 2/389; A61F 2310/0058; A61F 2310/00592; A61F 2310/00616; A61F 2310/00634; A61F 2310/0064; A61F 2310/00658; A61F 2310/00748; A61F 2310/00766; A61F 2310/00772; A61F 2310/0088; A61F 2310/00059; A61F 2310/00071; A61F 2310/00089; A61F 2310/00095; A61F 2310/00113; A61F 2310/00131; A61F 2310/00149; A61F 2310/00155; A61F 2/0077; A61F 2002/30321; A61F 2310/00023; A61F 2310/00011; A61F 2210/0014; A61F 2210/0076; A61B 17/58; A61B 17/00491; A61B 17/11; A61B 17/12022; A61B 17/12045; A61B 17/12136; A61B 17/1215; A61B 17/12172; A61B 17/12177; A61B 17/12186; A61B 17/1219; A61B 17/72; A61B 177/7275; A61B 17/746; A61B 17/80; A61B 17/8061; A61B 17/86; A61B 17/866; A61B 2017/00004; A61B 2017/22038; A61L 27/56; A61L 2420/08; A61L 2420/02; A61L 2420/06; A61L 27/04; A61L 27/06; A61L 27/507; A61L 31/08; A61L 31/022; A61L 31/14; C23C 16/56; C23C 18/1241; B21D 31/00; C22F 1/006; C22F 1/183; C22F 1/00
See application file for complete search history.

(56) References Cited

U.S. PATENT DOCUMENTS

| | | | |
|---|---|---|---|
| 6,238,491 B1 | 5/2001 | Davidson et al. | |
| 6,805,898 B1 | 10/2004 | Wu et al. | |
| 6,904,658 B2 | 6/2005 | Hines | |
| 6,938,668 B2 | 9/2005 | Whicher et al. | |
| 6,979,346 B1* | 12/2005 | Hossainy | A61F 2/91 623/1.11 |
| 7,122,049 B2 | 10/2006 | Banas et al. | |
| 2002/0114934 A1* | 8/2002 | Liu | C08F 2/44 428/212 |
| 2003/0004567 A1 | 1/2003 | Boyle et al. | |
| 2003/0074081 A1* | 4/2003 | Ayers | A61F 2/28 623/23.5 |
| 2004/0072124 A1* | 4/2004 | Kaufman | A61L 27/04 433/102 |
| 2004/0191404 A1 | 9/2004 | Hossainy et al. | |
| 2004/0241037 A1 | 12/2004 | Wu | |
| 2005/0059994 A1 | 3/2005 | Walak et al. | |
| 2005/0165467 A1 | 7/2005 | Hunter et al. | |
| 2005/0165468 A1 | 7/2005 | Marton | |
| 2005/0221258 A1* | 10/2005 | Hall | A61C 8/0012 433/173 |
| 2005/0228482 A1 | 10/2005 | Herzog et al. | |
| 2006/0002810 A1* | 1/2006 | Grohowski, Jr. | A61F 2/30767 419/2 |
| 2006/0116751 A1 | 6/2006 | Bayle et al. | |
| 2006/0155361 A1 | 7/2006 | Schomig et al. | |
| 2006/0259126 A1 | 11/2006 | Lenz | |
| 2007/0016283 A1 | 1/2007 | Greenhalgh et al. | |
| 2007/0061006 A1* | 3/2007 | Desatnik | C23C 16/06 623/1.42 |
| 2008/0035243 A1* | 2/2008 | Breitenkamp | A61L 27/04 148/240 |
| 2009/0005860 A1* | 1/2009 | Gale | A61F 2/91 623/1.44 |
| 2010/0248601 A1* | 9/2010 | McGrogan | B24D 13/147 451/526 |
| 2011/0127700 A1* | 6/2011 | Link | A61F 2/30767 264/662 |
| 2016/0250394 A1* | 9/2016 | Pawar | A61L 27/04 148/284 |
| 2017/0007743 A1* | 1/2017 | Hedrick | C23C 22/05 |

OTHER PUBLICATIONS

International Search Report and Written Opinion for PCT/US2009/039595 dated Jul. 1, 2010.
Summons to Attend Oral Proceedings Pursuant to Rule 115(1) EPC for European Patent Application No. EP 09730206.1, dated Apr. 24, 2012, pp. 1-5.

\* cited by examiner

SURFACE STRUCTURE OF A COMPONENT OF A MEDICAL DEVICE AND A METHOD OF FORMING THE SURFACE STRUCTURE

RELATED APPLICATIONS

The present patent document is a division of U.S. Non-provisional patent application Ser. No. 12/936,490, filed on Nov. 18, 2010, which is the national stage of International Application No. PCT/US2009/039595, filed on Apr. 6, 2009, which claims the benefit of priority under 35 U.S.C. 119(e) to U.S. Provisional Patent Application Ser. No. 61/043,279, filed on Apr. 8, 2008, all of which are hereby incorporated by reference in their entirety.

TECHNICAL FIELD

The present disclosure is related generally to medical devices, and more particularly to surfaces of components of medical devices.

BACKGROUND

Stents are generally designed as tubular support structures that can be used in a variety of medical procedures to treat blockages, occlusions, narrowing ailments and other problems that restrict flow through body vessels. Numerous vessels throughout the vascular system, including peripheral arteries, such as the carotid, brachial, renal, iliac and femoral arteries, and other body vessels, may benefit from treatment by stents. Self-expanding stents, which deploy automatically when released from an intraluminal delivery device, are often fabricated from superelastic materials such as equi-atomic or near-equiatomic nickel-titanium alloys (e.g., Nitinol).

A limiting factor in many stent designs is durability. For example, stents employed in the superficial femoral artery (SFA) may be exposed to significant axial, torsional and bending stresses. In addition, due to blood flow through the vessel, stents may experience pulsatile loading on the order of 400 million cycles over 10 years of in vivo use. Fatigue life is thus a critical consideration for stent design.

Although the fatigue mechanics of nickel-titanium alloys are quite complicated, it is generally accepted that surface flaws (cracks) are initiating sites for fatigue failure. It is believed that fatigue crack growth rates in nickel-titanium alloys are higher than crack growth rates in other titanium alloys used in medical devices. Small surface cracks in a stent structure have the propensity under some loading conditions to propagate until the structural integrity of the stent is compromised.

Consequently, the surfaces of nickel-titanium alloy stents are generally highly electropolished in an effort to mitigate the impact of surface flaws on device performance. Electropolishing may not be effective in eliminating all surface flaws, however. Fatigue life improvement remains a challenge for nickel-titanium alloy stent design.

BRIEF SUMMARY

Described herein is surface structure of a component of a medical device and a method of forming the surface structure. A nickel-titanium component that includes such a surface structure may have an improved resistance to fatigue failure and enhanced adhesion (e.g., bioadhesion) characteristics. The surface structure may also impart drug eluting capabilities to the component.

The surface structure of the component includes, according to one embodiment, a fatigue-resistant portion comprising a heat treated layer disposed on at least a portion of a surface of the component. The surface comprises a nickel-titanium alloy and the heat treated layer comprises a transition metal selected from the group consisting of Ta, Nb, Mo, V, Mn, Fe, Cr, Co, Ni, Cu, and Si. The surface structure also includes a rough outer surface of the fatigue-resistant portion, where the rough outer surface has an average roughness in the range of from about 0.1 micron to about 1000 microns.

The surface structure of the component includes, according to another embodiment, a fatigue-resistant portion comprising an alloyed region disposed on at least a portion of a surface of the component and a first layer comprising a transition metal disposed on the alloyed region. The surface comprises a nickel-titanium alloy, and the alloyed region comprises nickel, titanium, and the transition metal. The surface structure also includes a rough outer surface of the fatigue-resistant portion, where the rough outer surface has an average roughness in the range of from about 0.1 micron to about 1000 microns.

The method of forming the surface structure of the component includes forming a fatigue-resistant portion, which entails forming a first layer comprising a transition metal selected from the group consisting of Ta, Nb, Mo, V, Mn, Fe, Cr, Co, Ni, Cu, and Si on at least a portion of a surface of the component, where the surface comprises a nickel-titanium alloy, and alloying the transition metal of the first layer with the nickel-titanium alloy of the surface. The method further includes forming a rough outer surface of the fatigue-resistant portion, where the rough outer surface has an average roughness in the range of from about 0.1 micron to about 1000 microns.

DETAILED DESCRIPTION

Certain transition metals are known to be effective as beta-phase stabilizers in high strength beta-titanium alloys, such as Ti-13V-11Cr-3Al. The inventors believe that these transition metals may have a similarly advantageous effect when used for surface alloying of near-equiatomic nickel-titanium alloys, which are known to exhibit superelastic or shape memory behavior. Such alloys are commonly referred to as Nitinol or Nitinol alloys, and may be equiatomic (i.e., 50 at. % Ni and 50 at. % Ti) or near-equiatomic in composition.

In particular, the inventors have recognized that the fatigue strength of a Nitinol component of a medical device may be improved by heat treating a transition metal layer on the surface of the component and creating an alloyed interfacial region that is resistant to fatigue crack propagation, as described herein. Surprisingly, the fatigue resistance of the interfacial region is sufficiently high that an outer surface of the component may be intentionally roughened to enhance the adhesion (e.g., bioadhesion) characteristics of the surface without impairing the fatigue performance of the component. The roughened outer surface may also advantageously have drug eluting capabilities.

Figure 1:
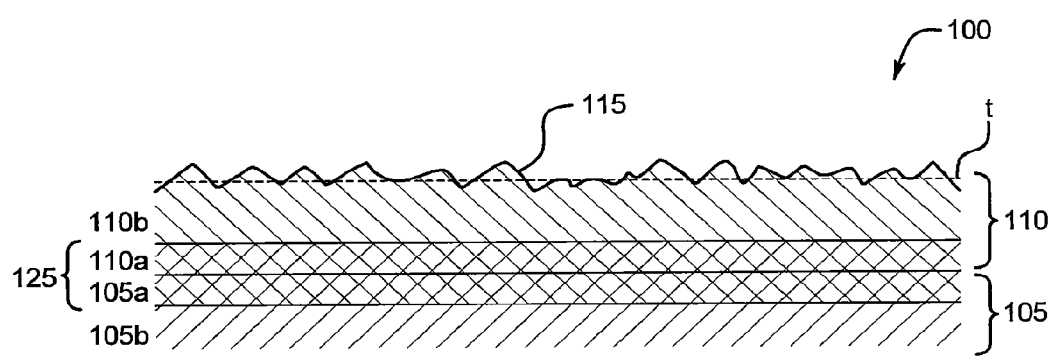
FIG. 1 is a cross-sectional schematic of a surface structure of a component of a medical device according to a first embodiment.

FIG. 1 shows in cross-section a surface structure 100 of a component of a medical device according to a first embodiment. The surface structure 100 includes a surface 105 comprising a nickel-titanium alloy and a heat treated layer 110 disposed on at least a portion of the surface 105. Preferably, the heat treated layer 110 covers substantially all of the surface 105. The heat treated layer 110 comprises a transition metal selected from the group consisting of Ta, Nb, Mo, V, Mn, Fe, Cr, Co, Ni, Cu, and Si. Preferably, the transition metal is Ta or Nb. The surface structure 100 preferably includes an interfacial region 125 that comprises an alloy of nickel, titanium, and the transition metal. The interfacial region generally encompasses an alloyed portion 105a of the surface 105 and an alloyed portion 110a of the heat treated layer 110. Accordingly, the interfacial region 125 is disposed between an unalloyed portion 110b of the heat treated layer 110 and an unalloyed portion 105b of the surface 105. The heat treated layer 110 includes a rough outer surface 115 that is adapted for biological attachment of body tissue (bioadhesion) and/or adhesion of additional layers. For example, the rough outer surface 115 of the heat treated layer 110 may contain protrusions and/or pores that permit body tissue to grow into or onto the layer 110.

Figure 2:
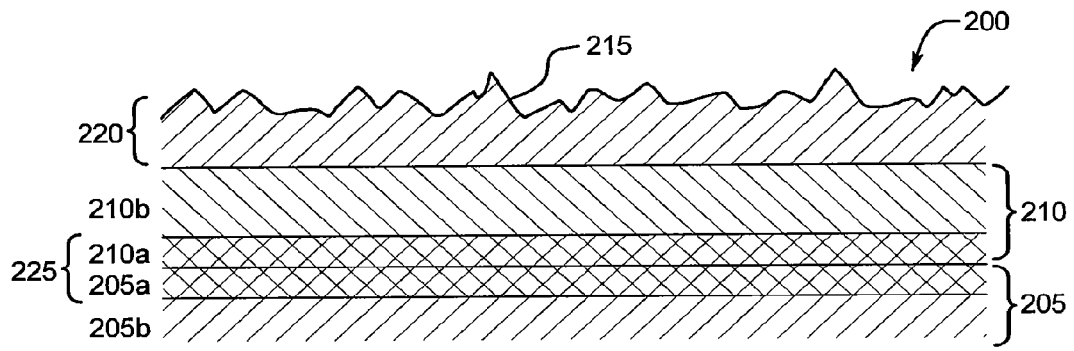
FIG. 2 is a cross-sectional schematic of a surface structure of a component of a medical device according to a second embodiment.

FIG. 2 shows a surface structure 200 of a component of a medical device according to a second embodiment. As in the first embodiment, the surface structure 200 includes a surface 205 of the component. The surface 205 comprises a nickel-titanium alloy and includes a heat treated layer 210 disposed on at least a portion of the surface 205, where the heat treated layer 210 comprises a transition metal selected from the group consisting of Ta, Nb, Mo, V, Mn, Fe, Cr, Co, Ni, Cu, and Si. Preferably, the transition metal is Ta or Nb. It is also preferred that the heat treated layer 210 covers substantially all of the surface 205. The surface structure 200 preferably includes an interfacial region 225, also as in the previous embodiment, that comprises an alloy of nickel, titanium, and the transition metal. The interfacial region generally encompasses an alloyed portion 205a of the surface 205 and an alloyed portion 210a of the heat treated layer 210 and is disposed between an unalloyed portion 210b of the heat treated layer 210 and an unalloyed portion 205b of the surface 205. According to the second embodiment, an additional layer 220 is disposed on the heat treated layer 210. The additional layer 220 includes a rough outer surface 215 that is adapted for adhesion of body tissue and/or further layers. For example, the rough outer surface 215 of the additional layer 220 may include protrusions and/or pores that are suited for biological attachment (bioadhesion) of tissue.

The first and second embodiments of the surface structures 100, 200 are described in detail below. Distinctions between the surface structures 100, 200 are noted; otherwise, similar elements of the surface structures are described collectively. It should be noted that the thickness of each of the various layers may include some lateral variations, although for the sake of simplicity the layers of FIGS. 1 and 2 show a substantially uniform thickness.

Preferably, the nickel-titanium alloy of the surface 105, 205 is superelastic. A superelastic nickel-titanium alloy undergoes a reversible phase transformation between a martensitic phase and an austenitic phase that allows it to "remember" and return to a previous shape or configuration. For example, compressive strain imparted to a martensitic stent to achieve a low-profile delivery configuration may be substantially recovered during a reverse phase transformation to austenite, such that the stent expands to a "remembered" (e.g., deployed) configuration at a treatment site in a vessel. Typically, recoverable strains of about 8-10% may be obtained from superelastic nickel-titanium alloys. The forward and reverse phase transformations may be driven by a change in stress (superelastic effect) and/or temperature (shape memory effect).

Slightly nickel-rich Nitinol alloys including, for example, about 51 at. % Ni and about 49 at. % Ti are known to be useful for medical devices which are superelastic at body temperature. In particular, alloys including 50.6-50.8 at. % Ni and 49.2-49.4 at. % Ti are considered to be medical grade Nitinol alloys and are suitable for the surface 105, 205 of the component. The nickel-titanium alloy may include one or more additional alloying elements. The surface 105, 205 may be either substantially flat or curved.

The heat treated layer 110, 210 is obtained by depositing a transition metal on the surface 105, 205 to form a first layer, and annealing (heat treating) the first layer at a temperature sufficient to cause alloying of the transition metal with the nickel-titanium alloy of the surface 105, 205. The first layer may be formed by physical vapor deposition (e.g., sputtering or thermal evaporation), chemical vapor deposition, electrodeposition or another suitable deposition technique. Preferably, the annealing is carried out after deposition of the first layer is complete. The heat treated layer 110, 210, including an alloyed portion 110a and an unalloyed portion 110b, is thus formed. The alloyed portion 110a is part of the interfacial region 125, 225, which comprises an alloy of nickel, titanium and the transition metal and is formed during the heat treatment. As noted above, the interfacial region 125, 225 preferably encompasses the alloyed portion 110a, 210a of the heat treated layer 110, 210 and an alloyed portion 105a, 205a of the surface 105, 205. Solid-state diffusion of the atoms from the heat treated layer into the surface, and of the atoms from the surface into the heat treated layer, is believed to be the mechanism for the alloying. The alloyed portion 105a, 205a of the surface 105, 205 includes transition metal atoms from the heat treated layer, and the alloyed portion 110a, 210a of the heat treated layer 110, 210 includes nickel and/or titanium atoms from the surface 105, 205.

The extent or thickness of the interfacial region 125, 225 generally depends on the temperature and time duration of the heat treatment. Preferably, the first layer is annealed at a temperature in the range of from about 800° C. to about 1100° C. The heat treatment may be carried out for a time duration of from about 1 minute to about 120 minutes. Preferably, the time duration is from about 1 minute to about 30 minutes. The atoms of the surface 105, 205 and the first layer may diffuse over distances of nanometers or microns to form the alloyed portions 105a, 205a, 110a, 210a that make up the interfacial region 125, 225.

The heat treated layer 110, 210 including the alloyed portion 110a, 210a is preferably about 200 microns or less in average thickness. For example, the heat treated layer 110, 210 may have an average thickness in the range of from about 0.1 micron (100 nanometers (nm)) to about 200 microns. The average thickness of the heat treated layer 110, 210 may also lie in the range of from about 1 micron to about 100 microns, or from about 5 microns to about 50 microns. According to the embodiment of FIG. 1, in which the rough outer surface 115 is part of the heat treated layer 110, the average thickness of the heat treated layer 110 is measured from the bottom surface of the alloyed portion 110a to the line t, which has a position corresponding to the mean distance between the highest protrusion and the deepest pore of the rough outer surface 115.

The alloyed portion 110a, 210a of the heat treated layer 110, 210 may have an average thickness of from about 0.05 micron (50 nm) to about 50 microns. Preferably, the average thickness is in the range of from about 0.5 micron (500 nm) to about 25 microns. Accordingly, the alloyed portion 110a, 210a of the heat treated layer 110, 210 may be a substantial portion thereof. For example, the alloyed portion 110a, 210a of the heat treated layer 110, 210 may have an average thickness equivalent to about 50% of the total thickness of the heat treated layer 110, 210, or less. In another example, the alloyed portion 110a, 210a of the heat treated layer 110, 210 may have an average thickness of about 20% of the total thickness of the heat treated layer 110, 210 or less. In yet another example, the alloyed portion 110a, 210a of the heat treated layer 110, 210 may have an average thickness of about 10% of the total thickness of the heat treated layer 110, 210, or about 1% of the total thickness of the heat treated layer 110, 210, or less.

The alloyed portion 105a, 205a of the surface 105, 205 may extend an average distance of from about 0.05 micron (50 nm) to about 50 microns into the surface 105, 205. Preferably, the alloyed portion 105a, 205a extends an average distance of from about 0.5 micron (500 nm) to about 25 microns into the surface 105, 205.

Accordingly, the interfacial region 125, 225, which includes the alloyed portion 105a, 205a of the surface 105, 205 and the alloyed portion 110a, 210a of the heat treated layer 110, 210, has an average thickness in the range of from about 0.1 micron (100 nm) to about 100 microns, according to one embodiment. The interfacial region 125, 225 preferably has an average thickness in the range of from about 1 micron to about 50 microns.

The interfacial region 125, 225 is believed to serve as a barrier to fatigue crack propagation. Accordingly, an outer surface of the component may be intentionally roughened to enhance adhesion thereto without compromising the fatigue behavior of the component. Preferably, the component has a fatigue life in the range of from about 10 million cycles to about 400 million cycles when under physiological loads.

Figure 3:
FIG. 3 is a cross-sectional schematic of an exemplary rough outer surface including only protrusions.
Figure 4:
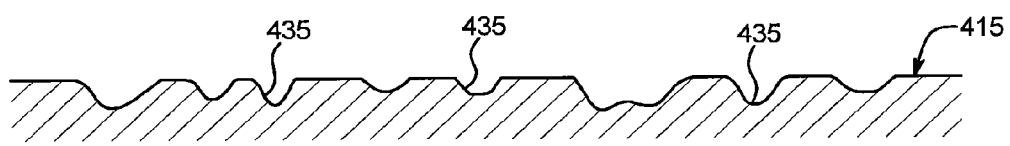
FIG. 4 is a cross-sectional schematic of an exemplary rough outer surface including only pores (or indentations)
Figure 5:
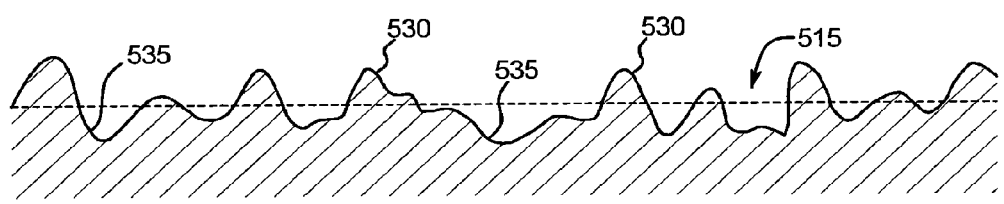
FIG. 5 is a cross-sectional schematic of an exemplary rough outer surface including both protrusions and pores (or indentations)

The rough outer surface 115, 215 may be suited for the attachment of body tissue (bioadhesion) and/or for the adherence of an additional layer, and may include one or both of protrusions and pores, as shown schematically in FIGS. 3-5. For example, FIG. 3 shows an exemplary rough outer surface 315 including only protrusions 330; FIG. 4 shows an exemplary rough outer surface 415 including only pores 435; and FIG. 5 shows an exemplary rough outer surface 515 including both protrusions 530 and pores 535.

The rough outer surface 115, 215 may be formed by mechanical abrasion or chemical etching of, in the case of the first embodiment, the heat treated layer 110 or, in the case of the second embodiment, the additional layer 220. For example, plasma etching, reactive ion etching, electrochemical etching, sand blasting or tumbling may be employed to provide the rough outer surface 115, 215.

Preferably, the rough outer surface 115, 215 has an average roughness $R_a$ suitable for promoting bioadhesion of adjacent tissue or adhesion of additional layers. The average roughness of the rough outer surface 115, 215 may lie in the range of from about 0.1 micron to about 1000 microns, for example, depending on whether the rough outer surface is intended for the in-growth/on-growth of tissue or for the adhesion of additional material layers. The average roughness of the outer surface 115, 215 may also lie in the range of from about 1 micron to about 500 microns, or from about 150 microns to about 350 microns. For the attachment of body tissue and to promote cellular in-growth, an average roughness of from about 25 microns to about 100 microns may be advantageous; pore sizes in this range have been found to be adequate for cell migration and growth (S. R. Bhattarai, *Biomaterials* 25 (2004) 2595-2602).

The average roughness may be determined using any of a number of known surface profiling or microscopy techniques, such as, for example, optical profilometry, stylus profilometry, scanning probe microscopy (SPM), or atomic force microscopy (AFM). Suitable surface profiling instrumentation may be obtained from Veeco Instruments Inc. (Woodbury, N.Y.), among other companies. Surface roughness measurements may be carried out in accordance with the ANSI/ASME B46.1 Surface Texture (Surface Roughness, Waviness, and Lay) standard, which is hereby incorporated by reference in its entirety.

Referring to FIG. 2, which shows a schematic of the surface structure 200 according to the second embodiment, an additional layer 220 may be disposed on the heat treated layer 210. According to this embodiment, the additional layer 220 includes the rough outer surface 215, which is adapted for adhesion of body tissue and/or further layers. As in the previous embodiment, the rough outer surface 215 preferably includes protrusions and/or pores (indentations) that facilitate attachment of body tissue and/or adhesion of additional layers.

Like the heat treated layer 210, the additional layer 220 may be formed of Ta, Nb, Mo, V, Mn, Fe, Cr, Co, Ni, Cu, or Si. Alternatively, the additional layer 220 may be formed of another biocompatible metal or alloy, such as, for example, nickel-titanium, stainless steel, cobalt-chromium, platinum, gold, or silver. Preferably, the additional layer 220 has an open, porous structure, where the rough outer surface 215 is a consequence of the porosity. The additional layer 220 may have an average thickness in the range of from about 0.1 micron to 100 microns. The average thickness may also range from about 1 micron to about 50 microns. The additional layer 220 may have a multilayered structure. For example, the additional layer 220 may include two or more layers.

According to one embodiment, the additional layer 220 is formed from sintered powder particles. The powder particles may be metals or alloys that are applied to the heat treated layer 210 in particulate form and then sintered to form the porous structure of the additional layer 220. The powder particles may include a binder that is substantially removed during the sintering process. The average size of the powder particles applied to the heat treated layer 210 may range from about 0.5 micron to about 50 microns. According to one embodiment, the average size of the powder particles ranges from about 5 microns to about 25 microns.

The sintering is generally carried out at a temperature in the range of from about 800° C. to about 1100° C. to form the additional layer 220. The powder particles may be applied to the first layer prior to the heat treatment that forms the alloyed interfacial region, and the sintering and the heat treatment may be carried out at the same time. Alternatively, the sintering may be carried out as a separate step, particularly if the desired sintering and heat treatment temperatures are different.

It is also contemplated that the additional layer 220 may include protrusions in addition to or instead of the pores. The surface roughening methods described above for mechanically abrading or chemically etching the heat treated layer 110 may be applied to the additional layer 220 to produce such a surface structure 200. For example, plasma etching, reactive ion etching, electrochemical etching, sand blasting or tumbling may be employed to provide a rough outer surface 215 of the additional layer 220 including pores and/or protrusions.

Due to its topology and increased surface area, the rough outer surface 115, 215 may advantageously provide drug eluting capabilities. For example, drug particles, proteins, peptides, genes or other biological molecules may be attached to or harbored within features of the rough outer surface 115, 215. Such biological materials, which may be generally referred to as "pharmaceutical agents," may be bound to or confined within pores or protrusions of the rough outer surface 115, 215. For example, a pharmaceutical agent such as paclitaxel may be bound to or otherwise incorporated into pores or indentations in the rough outer surface 115, 215 for the purpose of treating restenosis or other endoluminal conditions. Preferably, the pharmaceutical agent can be controllably released from the rough outer surface 115, 215 at an appropriate time or over a desired duration of time.

A medical device in accordance with the present disclosure includes at least one component having the improved surface structure described herein. The component may be formed from wire, tubing, ribbon, button, bar, disk, sheet, foil, or another pressed, cast, or worked shape. Preferably, the component is formed in whole or in part of a nickel-titanium alloy.

According to one embodiment, the component having the improved surface structure is a wire. According to another embodiment, the component is a tube or ring (i.e., "cannula"). The wire or cannula may be formed by extrusion and/or drawing methods known in the art. Gun drilling may be used to form a hole in an extruded or drawn cylinder. The cannula may also be produced by forming a sheet into a tubular configuration and welding the edges.

The component may be employed individually or in combination with other components to form an implantable medical device, such as, for example, a stent, a stent graft, a wire guide, a radiopaque marker or marker band, a torqueable catheter, an introducer sheath, an orthodontic arch wire, or a manipulation, retrieval, or occlusive device such as a grasper, a snare, a basket (e.g., stone extraction or manipulation basket), a vascular plug, an embolization coil, or an embolic protection filter.

Figure 6:
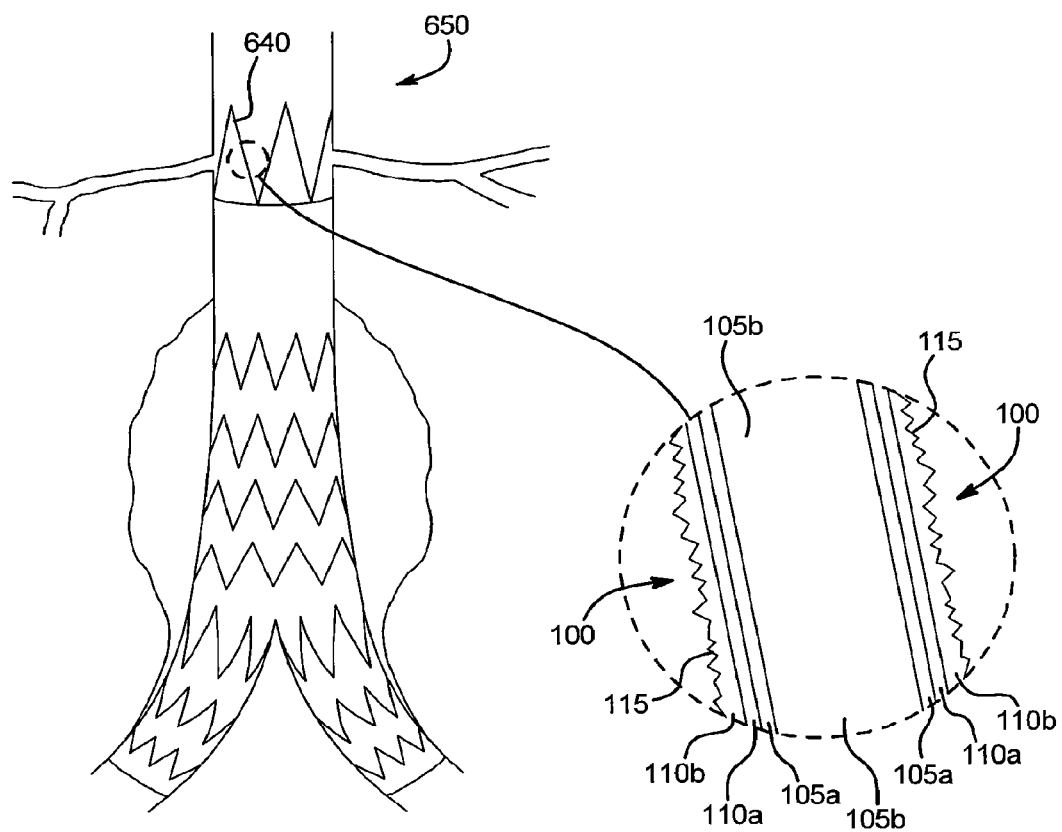
FIG. 6 is a schematic of a medical device at a treatment site, where the medical device includes a component having the surface structure of the first embodiment.

According to a preferred embodiment, the medical device including the component is a stent. The stent may be self-expanding or balloon-expandable. The stent may further include a graft material attached thereto. An exemplary stent graft 650 comprising a component (z-shaped wire) 640 having the improved surface structure 100 is shown schematically in FIG. 6.

Figure 7:
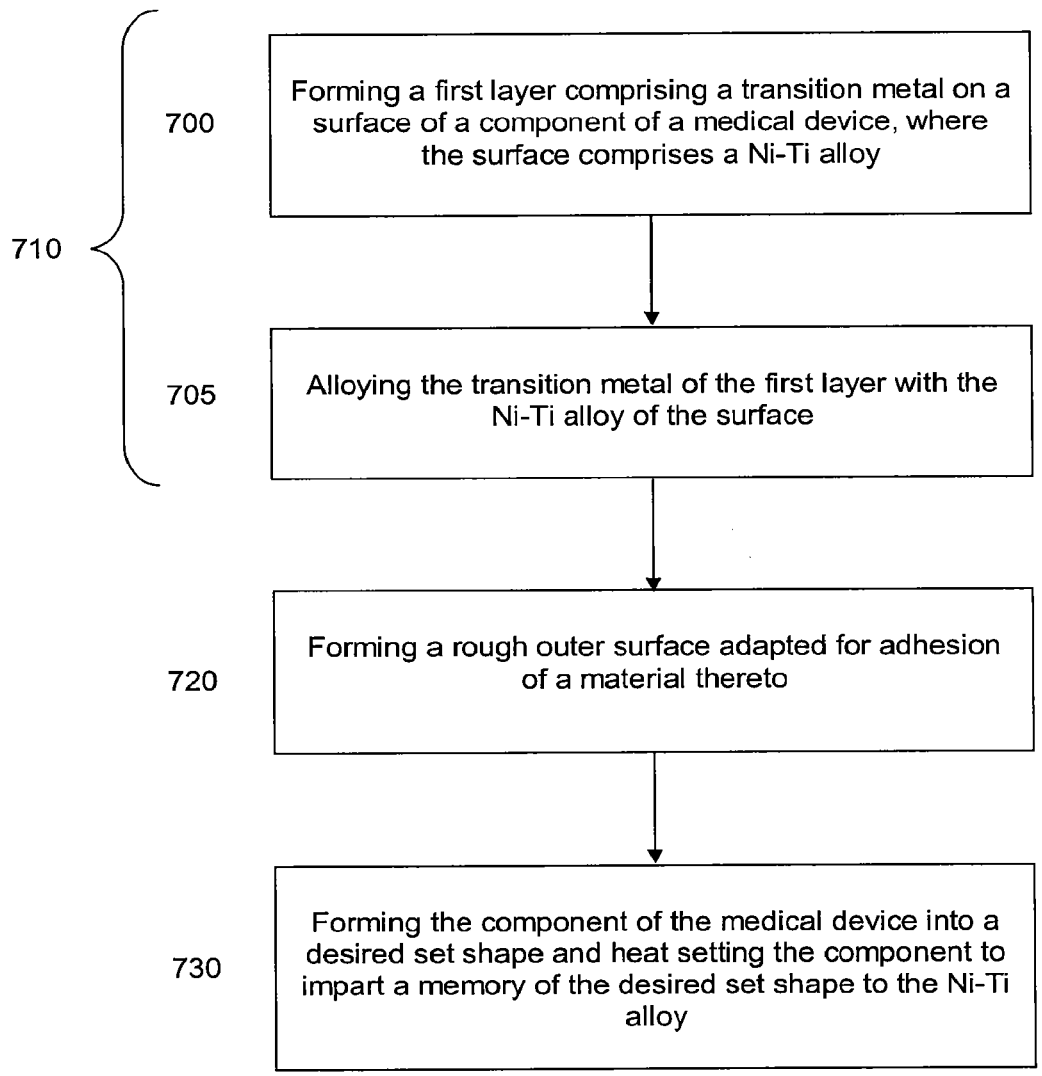
FIG. 7 is a flow chart showing steps of the method according to one embodiment.

Also described herein is a method of forming the surface structure of the component of the medical device. Referring to FIG. 7, the method includes forming 710 a fatigue-resistant portion, which entails forming 700 a first layer including a transition metal selected from the group consisting of Ta, Nb, Mo, V, Mn, Fe, Cr, Co, Ni, Cu, and Si on a surface of the component, where the surface of the component comprises a nickel-titanium alloy, and alloying 705 the transition metal of the first layer with the nickel-titanium alloy of the surface. The first layer may be formed 700 by physical vapor deposition (e.g., sputtering or thermal evaporation), chemical vapor deposition, electrodeposition or another suitable deposition technique. The alloying 705 may be carried out by heat treating (annealing) the first layer at a temperature in the range of from about 800° C. to 1100° C., as described previously. An interfacial region comprising an alloy of nickel, titanium, and the transition metal is thereby obtained. The alloyed interfacial region includes adjacent portions of the first layer and the surface.

A rough outer surface of the fatigue-resistant portion is then formed 720, where the rough outer surface is adapted for adhesion of a material thereto. Forming 720 the rough outer surface may entail roughening the first layer, as described previously. One or more of mechanical blasting, tumbling, electrochemical etching, plasma etching, and reactive ion etching may be employed to roughen the first layer.

Alternatively, an additional layer may be formed on the first layer, and the additional layer may provide the rough outer surface. To form the additional layer, a metallic powder may be deposited on the first layer and sintered at a temperature in the range of from about 800° C. to about 1100° C. The sintering may be carried out at the same time as the alloying, if desired, due to the compatibility of the heat treating and sintering temperatures. A porous layer having the desired surface roughness may thereby be obtained. It is also contemplated that the additional layer may be mechanically abraded or chemically etched as described above to obtain the rough outer surface.

The method may further entail forming 730 the component of the medical device into a desired set shape and heat setting the component at a temperature in the range of from about 350° C. to about 500° C. to impart a memory of the desired set shape to the nickel-titanium alloy. The desired set shape is preferably a deployed configuration of the component that may be "remembered" (recovered) once the medical device is in position at a treatment site in a body vessel. FIG. 7 indicates that the forming of the component and heat setting 730 are carried out after the forming of the rough outer surface 720, although it is contemplated that the rough outer surface may be formed 720 after the component has been formed and heat set 730.

A surface structure of a component of a medical device and a method of forming the surface structure have been described. The method may lead to an improvement in the fatigue life and adhesion (e.g., bioadhesion) characteristics of a nickel-titanium component. The method may also advantageously impart drug eluting capabilities to the component.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment.

What is claimed is:

1. A method of forming a surface structure of a component of a medical device, the method comprising:

forming a fatigue-resistant portion comprising forming a first layer comprising a transition metal selected from the group consisting of Ta, Nb, Mo, V, Mn, Fe, Cr, Co, Ni, Cu, and Si on at least a portion of a surface of the component, the surface comprising a nickel-titanium alloy, and alloying the transition metal of the first layer with the nickel-titanium alloy of the surface;

forming a rough outer surface of the fatigue-resistant portion, the rough outer surface having an average roughness of from about 150 microns to about 350 microns; and after alloying the transition metal of the first layer with the nickel-titanium alloy of the surface, forming the component of the medical device into a desired set shape and heat setting the component at a temperature in the range of from about 350° C. to about 500° C. to impart a memory of the desired set shape to the nickel-titanium alloy, thereby forming a superelastic nickel-titanium alloy configured to recover the desired set shape when the component is in position at a treatment site in a body vessel.

2. The method of claim 1, wherein forming the first layer comprising the transition metal comprises depositing a transition metal on the surface of the component by a deposition method selected from the group consisting of physical vapor deposition, chemical vapor deposition, and electrodeposition.

3. The method of claim 1, wherein alloying the transition metal of the first layer with the nickel-titanium alloy of the surface comprises heat treating the first layer at a temperature in the range of from about 800° C. to about 1100° C.

4. The method of claim 1, wherein forming the rough outer surface comprises forming an additional layer on the first layer, the additional layer comprising the average roughness of from about 150 microns to about 350 microns.

5. The method of claim 4, wherein forming the additional layer comprises depositing a metallic powder on the first layer and sintering the powder at a temperature in the range of from about 800° C. to about 1100° C.

6. The method of claim 1, wherein the forming of the component into the desired set shape and the heat setting of the component are carried out after the rough outer surface is formed.

7. The method of claim 1, wherein the forming of the component into the desired set shape and the heat setting of the component are carried out prior to forming the rough outer surface.

* * * * *